(12) United States Patent
Desconclois et al.

(10) Patent No.: US 6,548,506 B2
(45) Date of Patent: Apr. 15, 2003

(54) BENZO[1,8]NAPHTHYRIDINE DERIVATIVES, THEIR PREPARATION AND PHARMACEUTICAL COMPOSITIONS WHICH COMPRISE THEM

(75) Inventors: Jean-François Desconclois, Paris (FR); Guy Picaut, Villejuif (FR); Philippe Girard, Ollainville (FR); Michel Tabart, La Norville (FR); Sylvie Wentzler, Fresnes (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/884,127

(22) Filed: Jun. 20, 2001

(65) Prior Publication Data

US 2002/0037891 A1 Mar. 28, 2002

Related U.S. Application Data

(63) Continuation of application No. PCT/FR99/03206, filed on Dec. 20, 1999.
(60) Provisional application No. 60/138,582, filed on Jun. 11, 1999.

(30) Foreign Application Priority Data

Dec. 21, 1998 (FR) .............................. 98 16126

(51) Int. Cl.⁷ .................. A61K 31/496; A61K 31/4745; C07D 471/04; A61P 31/04
(52) U.S. Cl. ............. 514/253.03; 514/183; 514/211.08; 514/217.07; 514/292; 540/481; 540/575; 540/597; 544/361; 546/81
(58) Field of Search .............................. 546/81; 514/292, 514/183, 253.03, 211.08, 217.07; 540/481, 575, 597; 544/361

(56) References Cited

U.S. PATENT DOCUMENTS

| 5,004,745 A | 4/1991 | Antoine et al. |
| 5,053,509 A | 10/1991 | Antoine et al. |
| 5,556,861 A | 9/1996 | Bacque et al. |
| 5,688,791 A | * 11/1997 | Kimura ................... 514/224.5 |

FOREIGN PATENT DOCUMENTS

| EP | 0 379 412 | 7/1990 |
| EP | 0 431 991 | 6/1991 |
| EP | 0 536 035 | 4/1993 |

OTHER PUBLICATIONS

Derwent Abstract of EP 0379412.

* cited by examiner

*Primary Examiner*—Evelyn Mei Huang
(74) *Attorney, Agent, or Firm*—Finnegan, Henderson, Farabow, Garrett, & Dunner LLP

(57) ABSTRACT

Novel 1,8-benzo-naphthyridine derivatives of general formula (I):

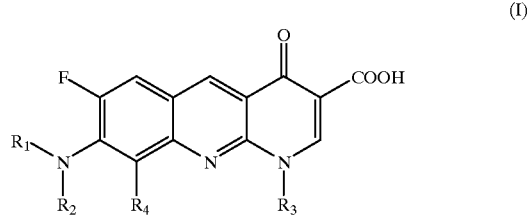

which are useful as antimicrobial agents.

22 Claims, No Drawings

BENZO[1,8]NAPHTHYRIDINE DERIVATIVES, THEIR PREPARATION AND PHARMACEUTICAL COMPOSITIONS WHICH COMPRISE THEM

This application is a continuation of International Application No. PCT/FR99/03206, filed on Dec. 20, 1999, and claims the priority of French Patent Application No. 98/16126, filed on Dec. 21, 1998, and the benefit of U.S. Provisional Application No. 60/138,582, filed on Jun. 11, 1999, the content of all of which is incorporated herein by reference.

The present invention is directed to novel benzo[b][1,8]-naphthyridine derivatives of general formula (I):

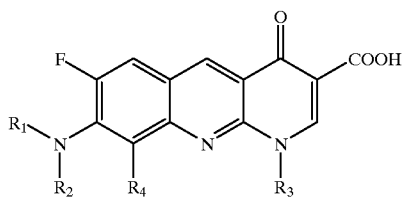

(I)

to their salts, to their preparation and to the compositions which comprise them.

Benzonaphthyridine derivatives with the structure:

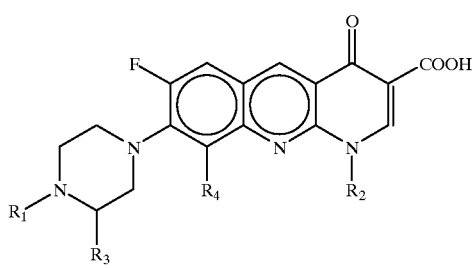

in which $R_1$ is H, hydroxyl or alkyl, $R_2$ is H, alkyl, fluoroalkyl, cycloalkyl, alkyloxy or alkylamino, $R_3$ is optionally substituted phenyl or phenylalkyl, and $R_4$ is H or a fluorine atom, have been disclosed in European Patent Application EP 431,991. These compounds are of use as antimicrobial agents.

It has now been found that the benzonaphthyridine derivatives of general formula (I) described below, as well as their salts and, when appropriate, their stereoisomers, display an antibacterial activity which is advantageous for topical administration. These benzonaphthyridine derivatives belong to the group of compounds of general formula (I) in which:

$R_1$ and $R_2$, which are identical or different, represent an alkyl or cycloalkyl radical comprising 3 to 8 members, or form, together with the nitrogen atom to which they are attached, a 6-membered heterocycle, optionally comprising another nitrogen atom, which can be substituted at the 4-position by a phenyl radical, a substituted phenyl radical (substituted by a halogen atom or by an alkylthiomethyl radical), a benzyl radical, a benzyl radical substituted by a halogen atom, a heterocyclylmethyl radical, the heterocyclyl part of which is saturated or unsaturated and comprises 5 or 6 members, a phenylamino radical or a phenylamino radical, the phenyl part of which is optionally substituted by a halogen atom, or $R_1$ and $R_2$ form, together with the nitrogen atom to which they are attached, a 7- or 8-membered heterocycle, optionally comprising another nitrogen atom, which can be substituted by one of the substituents of the 6-membered heterocycle listed above;

$R_3$ represents an alkyl radical, a fluoroalkyl radical, a carboxyalkyl radical, a cycloalkyl radical comprising 3 to 6 carbon atoms, a fluorophenyl radical, a difluorophenyl radical, an alkyloxy radical or an alkylamino radical; and $R_4$ represents a hydrogen atom or a fluorine atom;

the abovementioned alkyl radicals being straight or branched and comprising 1 to 4 carbon atoms.

In the above general formula, the halogen substituents can be chosen from chlorine, fluorine, bromine and iodine and the heterocyclyl radicals can be chosen from furyl, thienyl, pyridyl, pyrimidyl, imidazolyl, thiazolyl and pyrrolidyl. Furthermore, when $R_1$ and $R_2$ form, together with the nitrogen atom to which they are attached, a 6- to 8-membered heterocycle, the latter can be chosen without implied limitation from piperidine, piperazine, perhydroazepine, perhydroazocine, perhydrodiazepine, morpholine and thiomorpholine.

According to the invention, the compounds of general formula (I) can be obtained by substitution of an amine of general formula (II):

in which $R_1$ and $R_2$ are defined as above, with a benzo[b][1,8]naphythridine of general formula (III):

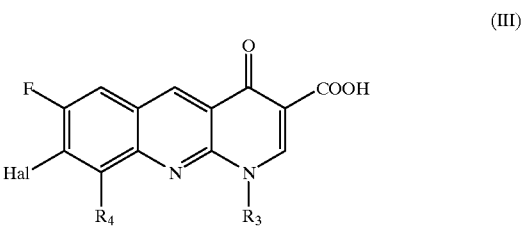

in which $R_3$ is defined as above, Hal is a fluorine, chlorine or bromine atom if $R_4$ is hydrogen, or else Hal and $R_4$ are simultaneously fluorine atoms.

The reaction of an amine of general formula (II) with the benzonaphythridine derivative is generally carried out in the presence of an excess of the benzonaphythridine derivative of general formula (III) as acid acceptor in suitable organic solvents. It is possible to carry out the reaction with or without solvent, at a temperature ranging from approximately 20 to approximately 150° C. When the reaction is carried out in the presence of a solvent, it can be carried out in solvents such as pyridine, dimethylformamide, dimethyl sulphoxide or acetonitrile. It is also possible to carry out the reaction in aqueous medium.

The reaction can also be carried out in the presence of an acid acceptor, such as, for example, a nitrogenous organic base, for example, triethylamine, an alkaline carbonate, for example, sodium carbonate, or an alkali metal or alkaline earth metal hydroxide.

According to the invention, the benzo[b][1,8]naphthyridine derivatives of general formula (I) can also be obtained from a corresponding ester of general formula (IV):

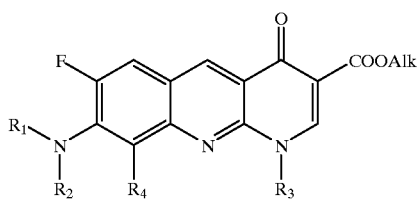

(IV)

in which $R_1$, $R_2$ and $R_4$ are defined as above, $R_3$ is defined as above or represents a protected alkylamino radical, and Alk represents an alkyl radical comprising 1 to 4 straight- or branched-chain carbon atoms, by any method known for producing an acid from an ester without affecting the remainder of the molecule.

The acid can be prepared from the ester by saponification in the presence of potassium hydroxide or sodium hydroxide, in aqueous or aqueous/alcoholic medium, at a temperature ranging from approximately 20 to approximately 100° C.; it is also possible to carry out the reaction by acid hydrolysis at temperatures such as mentioned above.

When $R_3$ represents a protected alkylamino radical, the protecting radical can be any amino-protecting group compatible with the molecule. It is possible to choose a protecting radical which can be removed simultaneously with the hydrolysis of the ester. Protection can be carried out by any compatible group, the use and the removal of which do not detrimentally affect the remainder of the molecule. The reaction can be carried out according to the methods described by T. W. Greene, (Protective Groups in Organic Synthesis, A. Wiley-Interscience Publication (1981)), or by McOmie, (Protective Groups in Organic Chemistry, Plenum Press (1973)), the relevant disclosure of each of which is hereby incorporated by reference.

The benzo[b][1,8]naphthyridine derivative of general formula (III) can be obtained by application of the methods disclosed in U.S. Pat. No. 4,990,515, or European patent No. EP 431,991 or EP 379,414, the relevant disclosure of each of which is hereby incorporated by reference, or by similar techniques.

The benzo[b][1,8]naphthyridine derivative of general formula (IV) can be obtained by reaction of an amine of general formula (II) with a corresponding ester of general formula (V):

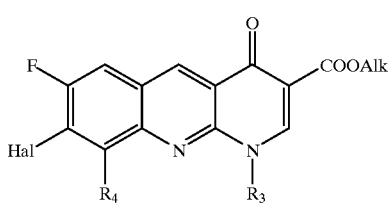

(V)

in which $R_3$, $R_4$, Hal and Alk are defined as above, according to the method described for the reaction of an amine of general formula (II) with the benzonaphthyridine derivative of general formula (III). It is understood that, in the alternative where the reaction is carried out in aqueous medium, it is possible to obtain a compound of general formula (I) directly without intermediate isolation of a derivative of general formula (IV).

The benzo[b][1,8]naphthyridine ester derivative of general formula (V) can be obtained as disclosed in European Patent No. EP 606,382, the relevant disclosure of which is incorporated herein by reference.

According to the invention, when stereoisomeric forms of the benzonaphthyridine derivatives of general formula (I) exist and when it is desired to obtain these stereoisomers, the stereoisomeric forms of the amines of general formula (II) can be separated by any known method compatible with the molecule. By way of example, the separation can be carried out by acylation with a chiral acid or a reactive derivative of a chiral acid, followed by separation of the isomers by high performance liquid chromatography, and then deacylation according to the method described by P. G. Gasseman et al., (J. Am. Chem. Soc., 98 (5), 1275 (1976)), the relevant disclosure of which is incorporated herein by reference. It is also possible to separate the stereoisomers by chiral phase high performance liquid chromatography.

The novel compounds according to the present invention and their synthetic intermediates can optionally be purified by physical methods, such as crystallization or chromatography.

The compounds according to the present invention and their intermediates of general formula (III) can be converted to metal salts or to addition salts with nitrogenous bases according to methods known per se. These salts can be obtained according to the usual methods, which do not detrimentally affect the remainder of the molecule, for example by the action of a metal base (e.g., alkali metal or alkaline earth metal base), ammonia or an amine of an abovementioned compound in an appropriate solvent, such as an alcohol, an ether or water, or by an exchange reaction with a salt of an organic acid. The salt formed precipitates after optional concentration of its solution and it is separated by filtration, sedimentation or lyophilization.

The novel compounds according to the invention can also be converted to addition salts with acids. The compounds of general formula (I) obtained in the form of these salts can be released and converted to salts of other acids according to the usual methods.

Mention may be made, as examples of pharmaceutically acceptable salts, of the salts with alkali metals (sodium, potassium or lithium) or with alkaline earth metals (magnesium or calcium), the ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine) and the addition salts with inorganic acids (hydrochlorides, hydrobromides, sulphates, nitrates or phosphates) or organic acids (succinates, fumarates, maleates, methanesulphonates, p-toluenesulphonates or isethionates).

The novel benzo[b][1,8]naphthyridine derivatives of general formula (I) according to the present invention and their pharmaceutically acceptable salts exhibit advantageous antibacterial properties. They display a remarkable in vitro and in vivo activity with regard to gram-positive microorganisms and with regard to microorganisms that are resistant to quinolones. Bearing in mind their activity, they are useful for topical administration.

In vitro, the compounds of general formula (I) have been shown to be active at a concentration ranging from about 0.06 to about 4 $\mu$g/cm$^3$ with regard to Staphylococcus aureus IP 8203 and at a concentration ranging from about 0.12 to about 4 $\mu$g/cm$^3$ with regard to Staphylococcus aureus N79, which is resistant to quinolones.

In vivo, the compound of Example 1 has been shown to be active at a concentration of about 2% in a cetomacrogol and benzyl alcohol formulation in the model of infection of the guinea-pig with *Staphylococcus aureus* ATCC 25923. It has also been shown to be active at about 2% with respect to the model of experimental infection of the guinea pig with *Staphylococcus aureus* AS 5155 strain, which is resistant to meticillin, $MLS_B$ and quinolones.

Finally, the compounds according to the invention do not exhibit toxicity at the doses used. After 2 weeks of topical application b.i.d. of a composition comprising the compound of Example 1 in the proportions of about 2, about 5 and about 10% to a rat, no toxic effect was observed. Likewise, after 2 weeks of topical application b.i.d. of a composition comprising the compound of Example 1 in the proportion of about 2% to the nasal mucous membrane of a rabbit, no toxic effect was observed either.

7-fluoro-8-[4-(4-fluorophenyl)piperazin-1-yl]-1-methyl-4-oxo-1,4-dihydrobenzo[b][1,8]naphthyridine-3-carboxylic acid and its salts are examples of useful compounds of general formula (I) in which:

$R_1$ and $R_2$, which are identical or different, represent an alkyl radical comprising 1 or 2 carbon atoms or a cyclopropyl radical, or form, together with the nitrogen atom to which they are attached, a 6-membered heterocycle, optionally comprising another nitrogen atom, which can be substituted at the 4-position by a phenyl radical, a phenyl radical substituted by a halogen atom or by a methylthiomethyl radical, a benzyl radical, a benzyl radical substituted by a halogen atom, a heterocyclylmethyl radical, the heterocyclyl part of which is unsaturated and comprises 5 members, or a phenylamino radical, the phenyl part of which is optionally substituted by a halogen atom, or $R_1$ and $R_2$ form, together with the nitrogen atom to which they are attached, a 7- or 8-membered heterocycle;

$R_3$ represents an alkyl radical comprising 1 or 2 carbon atoms, a cyclopropyl radical, a difluorophenyl radical or a methylamino radical; and $R_4$ represents a hydrogen atom or a fluorine atom; and their salts.

The following examples, given without implied limitation, illustrate the present invention.

EXAMPLE 1

7-Fluoro-8-[4-(4-fluorophenyl)piperazin-1-yl]-1-methyl-4-oxo-1,4-dihydrobenzo[b][1,8]-naphthyridine-3-carboxylic Acid:

A suspension of 5.0 g of 7,8-difluoro-1-methyl-4-oxo-1,4-dihydrobenzo[b][1,8]naphthyridine-3-carboxylic acid and 6.2 g of 4-(4-fluorophenyl)-piperazine in 30 cm³ of dimethyl sulphoxide was heated, with stirring, at a temperature around 90° C. for approximately 4 hours. After cooling to approximately 20° C., 25 cm³ of water were added to the reaction mixture. The insoluble material was filtered off and washed with 2 times 25 cm³ of water. After recrystallizing once from 150 cm³ of dimethylformamide, 7.6 g of 7-fluoro-8-[4-(4-fluorophenyl)piperazin-1-yl]-1-methyl-4-oxo-1,4-dihydrobenzo[b][1,8]naphthyridine-3-carboxylic acid were obtained in the form of a yellow solid melting at about 318-9° C.

Choline 7-fluoro-8-[4-(4-fluorophenyl)piperazin-1-yl]-1-methyl-4-oxo-1,4-dihydro-benzo[b][1,8] naphthyridine-3-carboxylate:

7.6 cm³ of a 45% solution of choline hydroxide in methanol were added to a suspension of 7.6 g of 7-fluoro-8-[4-(4-fluorophenyl)piperazin-1-yl]-1-methyl-4-oxo-1,4-dihydrobenzo[b][1,8]naphthyridine-3-carboxylic acid in 75 cm³ of methanol. The reaction mixture was stirred for approximately 2 hours at approximately 25° C. The solution was filtered in order to remove a slight insoluble material and was concentrated at approximately 50° C. on a rotary evaporator at approximately 20 kPa. The residual solid was recrystallized from 70 cm³ of 2-propanol and 30 cm³ of methanol. The crystals were filtered off with 10 cm³ of 2-propanol on each occasion and dried in an oven at 100° C. at 10 kPa. 7.4 g of choline 7-fluoro-8-[4-(4-fluorophenyl)piperazin-1-yl]-1-methyl-4-oxo-1,4-dihydrobenzo[b][1,8] naphthyridine-3-carboxylate were obtained in the form of a yellow solid melting at about 285-90° C.

7,8-Difluoro-1-methyl-4-oxo-1,4-dihydrobenzo[b][1,8] naphthyridine-3-carboxylic acid was prepared according to the method disclosed in European Patent No. EP-431,991.

EXAMPLE 2

7-Fluoro-8-[4-(4-fluorophenyl)piperazin-1-yl]-1-methyl-4-oxo-1,4-dihydrobenzo[b][1,8]-naphthyridine-3-carboxylic Acid:

A suspension of 3.07 g of 8-chloro-7-fluoro-1-methyl-4-oxo-1,4-dihydrobenzo[b][1,8]naphthyridine-3-carboxylic acid and 7.21 g of 4-(4-fluorophenyl)-piperazine in 30 cm³ of pyridine was heated at a temperature around 115° C. for 84 hours. The reaction mixture was concentrated under reduced pressure (20 kPa) at approximately 60° C. The solid obtained was taken up in 50 cm³ of water and 3.5 cm³ of 10% acetic acid were added. The suspension was brought to approximately 100° C. The solidified product was filtered off and washed 3 times with 30 cm³ and 3 times 30 cm³ of warm ethanol. After recrystallizing twice from 65 cm³ of dimethylformamide on each occasion, 2.82 g of 7-fluoro-8-[4-(4-fluorophenyl)piperazin-1-yl]-1-methyl-4-oxo-1,4-dihydrobenzo[b][1,8]naphthyridine-3-carboxylic acid were obtained in the form of a yellow solid melting at about 318–319° C.

8-Chloro-7-fluoro-1-methyl-4-oxo-1,4-dihydrobenzo[b][1,8]naphthyridine-3-carboxylic acid was prepared under the conditions disclosed in European Patent No. EP 431,991.

EXAMPLE 3

7-Fluoro-8-[4-(4-fluorophenyl)piperazin-1-yl]-1-methyl-4-oxo-1,4-dihydrobenzo[b][1,8]-naphthyridine-3-carboxylic Acid:

A suspension of 10.5 g of ethyl 7-fluoro-8-[4-(4-fluorophenyl)piperazin-1-yl]-1-methyl-4-oxo-1,4-dihydrobenzo[b][1,8]naphthyridine-3-carboxylate in 100 cm³ of acetic acid and 100 cm³ of 17.5% aqueous hydrochloric acid solution was heated, with stirring, at a temperature around 110° C. for approximately 4 hours. After cooling to approximately 20° C., 25 cm³ of water were added to the reaction mixture. The insoluble material was filtered off and washed 3 times with 200 cm³ of water and 2 times with 100 cm³ of ethanol. 9.3 g of 7-fluoro-8-[4-(4-fluorophenyl) piperazin-1-yl]-1-methyl-4-oxo-1,4-dihydrobenzo[b][1,8] naphthyridine-3-carboxylic acid were obtained in the form of a yellow solid melting at approximately 320° C., which solid was used without additional purification in the subsequent stages.

Ethyl 7-fluoro-8-[4-(4-fluorophenyl)piperazin-1-yl]-1-methyl-4-oxo-1,4-dihydrobenzo[b][1,8]naphthyridine-3-carboxylate was prepared by analogy to the method described in Example 1, from 3.2 g of ethyl 7,8-difluoro-1-methyl-4-oxo-1,4-dihydrobenzo[b][1,8]naphthyridine-3-carboxylate, 2.16 g of 4-(4-fluorophenyl)piperazine and 3.35 cm of triethylamine in 40 cm³ of dimethyl sulphoxide. After filtering off with 2 times 15 cm³ of water and 2 times 15 cm³ of ethanol, 0.4 g of ethyl 7-fluoro-8-[4-(4-fluorophenyl) piperazin-1-yl]-1-methyl-4-oxo-1,4-dihydrobenzo[b][1,8]

naphthyridine-3-carboxylate was obtained in the form of a yellow solid melting at about 310° C.

Ethyl 7,8-difluoro-1-methyl-4-oxo-1,4-dihydrobenzo[b][1,8]naphthyridine-3-carboxylate was prepared as disclosed in European Patent No. EP 431,991.

EXAMPLE 4

8-[(Cyclohexyl)(methyl)amino]-7-fluoro-1-methyl-4-oxo-1,4-dihydrobenzo[b][1,8]naphthyridine-3-carboxylic Acid:

8-[(Cyclohexyl)(methyl)amino]-7-fluoro-1-methyl-4-oxo-1,4-dihydrobenzo[b][1,8]naphthyridine-3-carboxylic acid was prepared under the conditions of Example 1, but from 1.5 g of 7,8-difluoro-1-methyl-4-oxo-1,4-dihydrobenzo[b][1,8]naphthyridine-3-carboxylic acid and 1.3 cm$^3$ of N-methylcyclohexylamine in 30 cm$^3$ of dimethyl sulphoxide. After washing 2 times with with 15 cm$^3$ of ethanol, 1.7 g of 8-[(cyclohexyl)(methyl)amino]-7-fluoro-1-methyl-4-oxo-1,4-dihydrobenzo[b][1,8]naphthyridine-3-carboxylic acid were obtained in the form of a yellow solid melting at about 265° C.

Choline 8-[(cyclohexyl)(methyl)amino]-7-fluoro-1-methyl-4-oxo-1,4-dihydrobenzo[b][1,8]naphthyridine-3-carboxylate:

Choline 8-[(cyclohexyl)(methyl)amino]-7-fluoro-1-methyl-4-oxo-1,4-dihydrobenzo[b][1,8]naphthyridine-3-carboxylate was prepared under the conditions of Example 1, but from 1.5 g of 8-[(cyclohexyl)(methyl)amino]-7-fluoro-1-methyl-4-oxo-1,4-dihydrobenzo[b][1,8]naphthyridine-3-carboxylic acid in 15 cm$^3$ of methanol and 1.5 cm$^3$ of a 45% solution of choline hydroxide in methanol. After recrystallizing from 15 cm$^3$ of 2-propanol, choline 8-[(cyclohexyl)(methyl)amino]-7-fluoro-1-methyl-4-oxo-1,4-dihydrobenzo[b][1,8]naphthyridine-3-carboxylate was obtained in the form of a yellow solid melting at about 245–250° C.

EXAMPLE 5

8-(Azocan-1-yl)-7-fluoro-1-methyl-4-oxo-1,4-dihydrobenzo[b][1,8]naphthyridine-3-carboxylic Acid:

8-(Azocan-1-yl)-7-fluoro-1-methyl-4-oxo-1,4-dihydrobenzo[b][1,8]naphthyridine-3-carboxylic acid was prepared under the conditions of Example 1, but from 1 g of 7,8-difluoro-1-methyl-4-oxo-1,4-dihydrobenzo[b][1,8]naphthyridine-3-carboxylic acid and 0.87 cm$^3$ of heptamethyleneimine in 20 cm$^3$ of dimethyl sulphoxide. After washing 2 times with 15 cm$^3$ of ethanol, 1.1 g of 8-(azocan-1-yl)-7-fluoro-1-methyl-4-oxo-1,4-dihydrobenzo[b][1,8]naphthyridine-3-carboxylic acid were obtained in the form of a yellow solid melting at about 320–325° C.

EXAMPLE 6

7-Fluoro-1-methyl-8-[4-[3-(methylsulphanylmethyl)phenyl]piperazin-1-yl]-4-oxo-1,4-dihydrobenzo[b][1,8]naphthyridine-3-carboxylic Acid:

7-Fluoro-1-methyl-8-[4-[3-(methylsulphanylmethyl)phenyl]piperazin-1-yl]-4-oxo-1,4-dihydrobenzo[b][1,8]naphthyridine-3-carboxylic acid was prepared under the conditions of Example 1, but from 0.45 g of 7,8-difluoro-1-methyl-4-oxo-1,4-dihydrobenzo[b][1,8]naphthyridine-3-carboxylic acid and 0.66 g of [3-(methylsulphanylmethyl)phenyl]piperazine in 15 cm$^3$ of dimethyl sulphoxide. After washing 2 times with 15 cm$^3$ of ethanol, 0.61 g of 7-fluoro-1-methyl-8-[4-[3-(methylsulphanylmethyl)phenyl]piperazin-1-yl]-4-oxo-1,4-dihydrobenzo-[b][1,8]naphthyridine-3-carboxylic acid was obtained in the form of a yellow solid melting at about 240–5° C.

[3-(Methylsulphanylmethyl)phenyl]piperazine was prepared according to the following method:

A mixture of 2.5 g of 1-iodo-3-(methylsulphanylmethyl)benzene, 1.3 g of sodium tert-butoxide, 0.35 mg of [1,1'-bis(diphenylphosphino)ferrocenyl]palladium chloride, 0.79 g of 1,1'-bis(diphenylphosphino)ferrocene, 4 g of piperazine and 100 cm$^3$ of toluene was heated at 900° C. under a nitrogen stream for 24 hours. The reaction mixture was cooled to room temperature and filtered through sintered glass. The filtrate was washed with 250 cm$^3$ of dichloromethane and then concentrated to dryness under reduced pressure (2.7 kPa). The residue obtained was purified by silica gel column chromatography (particle size 0.04–0.06 mm, diameter 4 cm, height 20 cm) under a pressure of 0.5 bar of nitrogen with a mixture of dichloromethane and methanol (90/10 by volume) and then a mixture of dichloromethane and methanol (85/15 by volume) as eluents, 100-cm$^3$ fractions were collected. Fractions 29 to 36 were combined and concentrated to dryness under reduced pressure (2.7 kPa). The oil obtained was distilled in a bulb oven (B.p.=160° C. approximately under a pressure of 0.1 mm of mercury). 0.67 g of 4-[3-(methylsulphanylmethyl)phenyl]piperazine was obtained in the form of a colorless oil.

EXAMPLE 7

7-Fluoro-8-[4-(4-fluoroanilino)piperidino]-1-methyl-4-oxo-1,4-dihydrobenzo[b][1,8]naphthyridine-3-carboxylic Acid:

7-Fluoro-8-[4-(4-fluoroanilino)piperidino]-1-methyl-4-oxo-1,4-dihydrobenzo[b][1,8]naphthyridine-3-carboxylic acid was prepared under the conditions of Example 2, but from 1.6 g of 8-chloro-7-fluoro-1-methyl-4-oxo-1,4-dihydrobenzo[b][1,8]naphthyridine-3-carboxylic acid and 3.7 g of 4-(4-fluoroanilino)-piperidine in 16 cm$^3$ of pyridine. After recrystallizing from 10 cm$^3$ of dimethylformamide, 1.65 g of 7-fluoro-8-[4-(4-fluoroanilino)piperidino]-1-methyl-4-oxo-1,4-dihydrobenzo[b][1,8]naphthyridine-3-carboxylic acid were obtained in the form of a yellow solid melting at about 280° C.

Choline 7-fluoro-8-[4-(4-fluoroanilino)piperidino]-1-methyl-4-oxo-1,4-dihydrobenzo[b][1,8]naphthyridine-3-carboxylate:

Choline 7-fluoro-8-[4-(4-fluoroanilino)piperidino]-1-methyl-4-oxo-1,4-dihydro-benzo[b][1,8]naphthyridine-3-carboxylate was prepared under the conditions of Example 1, but from 1.6 g of 7-fluoro-8-[4-(4-fluoroanilino)piperidino]-1-methyl-4-oxo-1,4-dihydrobenzo[b][1,8]naphthyridine-3-carboxylic acid in 16 cm$^3$ of methanol and 1.3 cm$^3$ of a 45% solution of choline hydroxide in methanol. After recrystallizing twice from 25 cm$^3$ of 2-propanol on each occasion, 1.1 g of choline 7-fluoro-8-[4-(4-fluoroanilino)piperidino]-1-methyl-4-oxo-1,4-dihydrobenzo[b][1,8]naphthyridine-3-carboxylate were obtained in the form of a yellow solid melting at about 200–205° C.

4-(4-Fluoroanilino)piperidine was prepared according to U.S. Pat. No. 3,686,187, the relevant disclosure of which is herein incorporated by reference.

EXAMPLE 8

7-Fluoro-8-[4-(4-fluorobenzyl)piperazin-1-yl]-1-methyl-4-oxo-1,4-dihydrobenzo[b][1,8]naphthyridine-3-carboxylic Acid:

7-Fluoro-8-[4-(4-fluorobenzyl)piperazin-1-yl]-1-methyl-4-oxo-1,4-dihydrobenzo[b][1,8]naphthyridine-3-carboxylic acid was prepared under the conditions of Example 2, but from 1.6 g of 8-chloro-7-fluoro-1-methyl-4-oxo-1,4-dihydrobenzo[b][1,8]naphthyridine-3-carboxylic acid and 5 g of 4-(4-fluorobenzyl)piperazine in 16 cm$^3$ of pyridine.

After recrystallizing twice from 25 cm$^3$ of dimethylformamide on each occasion, 1.4 g of 7-fluoro-8-[4-(4-fluorobenzyl)piperazin-1-yl]-1-methyl-4-oxo-1,4-dihydrobenzo[b][1,8]naphthyridine-3-carboxylic acid were obtained in the form of a yellow solid melting at about 311° C.

EXAMPLE 9
7-Fluoro-8-[4-benzylpiperazin-1-yl]-1-methyl-4-oxo-1,4-dihydrobenzo[b][1,8]-naphthyridine-3-carboxylic Acid:

7-Fluoro-8-[4-benzylpiperazin-1-yl]-1-methyl-4-oxo-1,4-dihydrobenzo[b][1,8]-naphthyridine-3-carboxylic acid was prepared under the conditions of Example 2, but from 2 g of 8-chloro-7-fluoro-1-methyl-4-oxo-1,4-dihydrobenzo[b][1,8]naphthyridine-3-carboxylic acid and 4.6 g of N-benzylpiperazine in 20 cm$^3$ of pyridine. After recrystallizing twice from 25 cm$^3$ of dimethylformamide on each occasion, 1.4 g of 7-fluoro-8-[4-benzylpiperazin-1-yl]-1-methyl-4-oxo-1,4-dihydrobenzo[b][1,8]naphthyridine-3-carboxylic acid were obtained in the form of a yellow solid melting at about 311° C.

EXAMPLE 10
1-Ethyl-7-fluoro-8-[4-(4-fluorophenyl)piperazin-1-yl]-4-oxo-1,4-dihydrobenzo[b][1,8]-naphthyridine-3-carboxylic Acid:

1-Ethyl-7-fluoro-8-[4-(4-fluorophenyl)piperazin-1-yl]-4-oxo-1,4-dihydrobenzo-[b][1,8]naphthyridine-3-carboxylic acid was prepared under the conditions of Example 2, but from 1.75 g of 8-chloro-1-ethyl-7-fluoro-4-oxo-1,4-dihydrobenzo[b][1,8]naphthyridine-3-carboxylic acid and 3.6 g of 4-(4-fluorophenyl)piperazine in 18 cm$^3$ of pyridine. The solid obtained was taken up in 10 cm$^3$ of water and 1.9 cm$^3$ of 10% acetic acid were added. The suspension was brought to approximately 100° C. The solidified product was filtered off and washed 2 times with 10 cm$^3$ of water and 2 times with 10 cm$^3$ of warm ethanol. After recrystallizing twice from 25 cm$^3$ of dimethylformamide on each occasion, 1.7 g of 1-ethyl-7-fluoro-8-[4-(4-fluorophenyl)piperazin-1-yl]-4-oxo-1,4-dihydrobenzo[b][1,8]naphthyridine-3-carboxylic acid were obtained in the form of a pinkish-beige solid melting at about 311–312° C.

EXAMPLE 11
1-Ethyl-7-fluoro-8-[4-(4-fluorobenzyl)piperazin-1-yl]-4-oxo-1,4-dihydrobenzo[b][1,8]-naphthyridine-3-carboxylic Acid:

1-Ethyl-7-fluoro-8-[4-(4-fluorobenzyl)piperazin-1-yl]-4-oxo-1,4-dihydrobenzo-[b][1,8]naphthyridine-3-carboxylic acid was prepared under the conditions of Example 2, LAW OFFICES but from 1.6 g of 8-chloro-1-ethyl-7-fluoro-4-oxo-1,4-dihydrobenzo[b][1,8]naphthyridine-3-carboxylic acid and 3.9 g of 4-(4-fluorobenzyl)piperazine. After recrystallizing twice from 20 cm$^3$ of dimethylformamide on each occasion, 1.4 g of 1-ethyl-7-fluoro-8-[4-(4-fluorobenzyl)piperazin-1-yl]-4-oxo-1,4-dihydrobenzo[b][1,8]naphthyridine-3-carboxylic acid were obtained in the form of a yellow solid melting at about 286-8° C.

EXAMPLE 12
1-Cyclopropyl-7,9-difluoro-8-(4-furfurylpiperazin-1-yl)-4-oxo-1,4-dihydrobenzo[b][1,8]-naphthyridine-3-carboxylic Acid:

A suspension of 1.5 g of ethyl 1-cyclopropyl-7,9-difluoro-8-(4-furfurylpiperazin-1-yl)-4-oxo-1,4-dihydrobenzo[b][1,8]naphthyridine-3-carboxylate was heated, with stirring, at a temperature around 80° C. for approximately 1 hour 30 in 15 cm$^3$ of ethanol and 14 cm$^3$ of 1 N potassium hydroxide solution, 32 cm$^3$ of 5% acetic acid were added at this same temperature and the suspension was stirred for 20 minutes. After recrystallizing from a mixture of 15 cm$^3$ of dimethylformamide and 15 cm$^3$ of ethanol, 0.7 g of 1-cyclopropyl-7,9-difluoro-8-(4-furfurylpiperazin-1-yl)-4-oxo-1,4-dihydrobenzo[b][1,8]-naphthyridine-3-carboxylic acid was obtained in the form of a yellow solid melting at about 241° C.

Ethyl 1-cyclopropyl-7,9-difluoro-8-(4-furfurylpiperazin-1-yl)-4-oxo-1,4-dihydrobenzo[b][1,8]naphthyridine-3-carboxylate was prepared under the conditions of Example 3, but from 1.8 g of ethyl 1-cyclopropyl-7,8,9-trifluoro-4-oxo-1,4-dihydrobenzo-[b][1,8]naphthyridine-3-carboxylate and 4.8 g of 4-furfurylpiperazine hydrochloride in 30 cm$^3$ of dimethyl sulphoxide and 5.2 cm$^3$ of triethylamine. 1.5 g of ethyl 1-cyclopropyl-7,9-difluoro-8-(4-furfurylpiperazin-1-yl)-4-oxo-1,4-dihydrobenzo[b][1,8]naphthyridine-3-carboxylate were obtained in the form of a yellow-brown solid melting at about 125–128° C., which solid was used without additional purification in the subsequent stages.

Ethyl 1-cyclopropyl-7,8,9-trifluoro-4-oxo-1,4-dihydrobenzo[b][1,8]naphthyridine-3-carboxylate can be prepared as disclosed in European Patent No. EP 431,991.

4-Furfurylpiperazine hydrochloride was prepared according to the method described by M. Pesson et al., (Eur. J. Med. Chim. Ther., 10:567–570 (1975)).

EXAMPLE 13
7,9-Difluoro-1-(2,4-difluorophenyl)-8-[4-(4-fluorophenyl)piperazin-1-yl]-4-oxo-1,4-dihydrobenzo[b][1,8] naphthyridine-3-carboxylic Acid:

A suspension of 1.2 g of ethyl 7,9-difluoro-1-(2,4-difluorophenyl)-8-[4-(4-fluorophenyl)piperazin-1-yl]-4-oxo-1,4-dihydrobenzo[b][1,8]naphthyridine-3-carboxylate in 15 cm$^3$ of ethanol and 16 cm$^3$ of 1N aqueous potassium hydroxide solution was heated with stirring at a temperature around 80° C. for 2 hours. 10 cm$^3$ of a 10% aqueous acetic acid solution were added, at approximately 80° C., to the solution obtained. The insoluble material was filtered off at this temperature, washed 2 times with 30 cm$^3$ of water and recrystallized from a mixture of 12.5 cm$^3$ of ethanol and 12.5 cm$^3$ of dimethylformamide. 0.75 g of 7,9-difluoro-1-(2,4-difluorophenyl)-8-[4-(4-fluorophenyl)piperazin-1-yl]-4-oxo-1,4-dihydrobenzo[b][1,8]naphthyridine-3-carboxylic acid was obtained in the form of a yellow solid melting at about 284–286° C.

Ethyl 7,9-difluoro-1-(2,4-difluorophenyl)-8-[4-(4-fluorophenyl)piperazin-1-yl]-4-oxo-1,4-dihydrobenzo[b][1,8]naphthyridine-3-carboxylate was prepared under the following conditions:

A suspension of 1.5 g of ethyl 1-(2,4-difluorophenyl)-7,8,9-trifluoro-4-oxo-1,4-dihydrobenzo[b][1,8]naphthyridine-3-carboxylate and 1.8 g of 4-(4-fluorophenyl)piperazine in 20 cm$^3$ of dimethyl sulphoxide was heated, with stirring, at a temperature around 100° C. for approximately 1 hour. After cooling to approximately 20° C., the reaction mixture was poured into 100 cm$^3$ of water and extracted 3 times with 50 cm$^3$ of trichloromethane. The combined organic extracts were washed 1 time with 50 cm$^3$ of water, dried over magnesium sulphate and concentrated under reduced pressure (20 kPa) at a temperature around 40° C. 1.7 g of ethyl 7,9-difluoro-1-(2,4-difluorophenyl)-8-[4-(4-fluorophenyl) piperazin-1-yl]-4-oxo-1,4-dihydrobenzo[b][1,8] naphthyridine-3-carboxylate were obtained in the form of a yellow solid melting at about 298–299° C., which solid was used without additional purification in the subsequent stages.

Ethyl 1-(2,4-difluorophenyl)-7,8,9-trifluoro-4-oxo-1,4-dihydrobenzo[b][1,8]naphthyridine-3-carboxylate was prepared in the following way:

5.2 g of 2,4-difluoroaniline were added, at a temperature around 20° C., to a solution of 7.7 g of ethyl 3-(2-chloro-6,7,8-trifluoro-3-quinolyl)-2-dimethylaminomethylene-3-oxopropionate in 50 cm³ of trichloromethane and the reaction mixture was left stirring at this temperature for 8 hours. The trichloromethane was concentrated under reduced pressure (20 kPa) at a temperature around 40° C. 120 cm³ of ethanol and 4.5 cm³ of 1,8-diazabicyclo[5.4.0]undec-7-ene were added to the mixture, which was heated at a temperature around 80° C. for approximately 1 hour. After cooling to a temperature around 10° C., the product was filtered off and washed 2 times with 50 cm³ of ethanol and 2 times with 50 cm³ of isopropyl ether. 5 g of ethyl 1-(2,4-difluorophenyl)-7,8,9-trifluoro-4-oxo-1,4-dihydrobenzo[b][1,8]naphthyridine-3-carboxylate were obtained in the form of a yellow solid melting at about 304–306° C., which solid was used without additional purification in the subsequent stages.

Ethyl 3-(2-chloro-6,7,8-trifluoro-3-quinolyl)-2-dimethylaminomethylene-3-oxopropionate is disclosed in European Patent No. EP 431,991.

EXAMPLE 14

7-Fluoro-8-[4-(4-fluorophenyl)piperazin-1-yl]-1-methylamino-4-oxo-1,4-dihydrobenzo[b][1,8]naphthyridine-3-carboxylic Acid:

7-Fluoro-8-[4-(4-fluorophenyl)piperazin-1-yl]-1-methylamino-4-oxo-1,4-dihydrobenzo[b][1,8]naphthyridine-3-carboxylic acid was prepared under the conditions of Example 2, but from 3.2 g of 8-chloro-7-fluoro-1-methylamino-4-oxo-1,4-dihydrobenzo[b][1,8]naphthyridine-3-carboxylic acid and 9 g of 4-(4-fluorophenyl)piperazine in 30 cm³ of pyridine for 28 hours. After concentrating the reaction mixture to dryness under reduced pressure (20 kPa) at approximately 60° C., the residue was taken up twice in 30 cm³ of ethanol and concentrated under reduced pressure under the above conditions. The solid was taken up into 50 cm³ of water and 10 cm³ of 30% aqueous potassium hydroxide solution. 20 cm³ of water and approximately 10 cm³ of 10% acetic acid were added to the precipitate formed. The suspension was extracted 3 times with 50 cm³ of trichloromethane. The trichloromethane was concentrated under reduced pressure (20 kPa) and the solid obtained was taken up in 2 times 20 cm³ of ethanol. After crystallizing once from 42 cm³ and then recrystallizing once from 15 cm³ of dimethylformamide, 1.33 g of 7-fluoro-8-[4-(4-fluorophenyl)piperazin-1-yl]-1-methylamino-4-oxo-1,4-dihydrobenzo[b][1,8]naph-thyridine-3-carboxylic acid were obtained in the form of a brown solid melting at about 304–305° C.

8-Chloro-7-fluoro-1-methylamino-4-oxo-1,4-dihydrobenzo[b][1,8]naphthyridine-3-carboxylic acid is disclosed in European Patent No. EP 379,414.

EXAMPLE 15

1-Cyclopropyl-7-fluoro-8-[4-(4-fluoroanilino)piperidino]-4-oxo-1,4-dihydrobenzo[b][1,8]-naphthyridine-3-carboxylic Acid:

A suspension of 1.2 g of ethyl 1-cyclopropyl-7-fluoro-8-[4-(4-fluoroanilino)piperidino-4-oxo-1,4-dihydrobenzo[b][1,8]naphthyridine-3-carboxylate in 20 cm³ of acetic acid and 20 cm³ of 17.5% aqueous hydrochloric acid solution was heated with stirring at a temperature around 110° C. for 4 hours. After cooling to approximately 20° C., 30 cm³ of a 15% aqueous sodium hydroxide solution were added to the solution. The insoluble material was filtered off, washed 2 times with 30 cm³ of water and recrystallized from a mixture of 50 cm³ of ethanol and 60 cm³ of dimethylformamide. 1 g of 1-cyclopropyl-7-fluoro-8-[4-(4-fluoroanilino)piperidino]-4-oxo-1,4-dihydrobenzo[b][1,8]naphthyridine-3-carboxylic acid was obtained in the form of a yellow solid melting at about 295° C.

Ethyl 1-cyclopropyl-7-fluoro-8-[4-(4-fluoroanilino)piperidino-4-oxo-1,4-dihydrobenzo[b][1,8]naphthyridine-3-carboxylate was prepared under the following conditions: a suspension of 2.8 g of ethyl 8-chloro-1-cyclopropyl-7-fluoro-4-oxo-1,4-dihydrobenzo[b][1,8]naphthyridine-3-carboxylate and 6 g of 4-(4-fluoroanilino)piperidine in 80 cm³ of dimethyl sulphoxide was heated, with stirring, at a temperature around 110° C. for approximately 10 hours. After cooling to approximately 20° C., the reaction mixture was concentrated under reduced pressure (20 kPa) at a temperature around 140° C. The black residue was recrystallized from a mixture of 75 cm³ of ethanol and 35 cm³ of dimethylformamide. 2.35 g of ethyl 1-cyclopropyl-7-fluoro-8-[4-(4-fluoroanilino)-piperidino-4-oxo-1,4-dihydrobenzo[b][1,8]naphthyridine-3-carboxylate were obtained in the form of a brown solid melting at approximately 230° C., which solid was used without additional purification in the subsequent stages.

Ethyl 8-chloro-1-cyclopropyl-7-fluoro-4-oxo-1,4-dihydrobenzo[b][1,8]naphthyridine-3-carboxylate is disclosed in European Patent No. EP 431,991.

EXAMPLE 16

1-(2,4-Difluorophenyl)-7-fluoro-8-[4-(4-fluorophenyl)piperazin-1-yl]-4-oxo-1,4-dihydro-benzo[b][1,8]naphthyridine-3-carboxylic Acid:

1-(2,4-Difluorophenyl)-7-fluoro-8-[4-(4-fluorophenyl)piperazin-1-yl]-4-oxo-1,4-dihydrobenzo[b][1,8]naphthyridine-3-carboxylic acid was prepared under the conditions of Example 1, but from 1.55 g of 7,8-difluoro-1-(2,4-difluorophenyl)-4-oxo-1,4-dihydrobenzo[b][1,8]naphthyridine-3-carboxylic acid and 1.58 g of 4-(4-fluorophenyl)piperazine in 15 cm³ of dimethyl sulphoxide. After recrystallizing once from 55 cm³ of dimethylformamide, 1.4 g of 1-(2,4-difluorophenyl)-7-fluoro-8-[4-(4-fluorophenyl)piperazin-1-yl]-4-oxo-1,4-dihydrobenzo[b][1,8]naphthyridine-3-carboxylic acid were obtained in the form of a yellow solid melting at about 322° C.

7,8-Difluoro-1-(2,4-difluorophenyl)-4-oxo-1,4-dihydrobenzo[b][1,8]naphthyridine-3-carboxylic acid was obtained under the conditions described in Example 3, but from 3.2 g of ethyl 1-(2,4-difluorophenyl)-7-fluoro-8-[4-(4-fluorophenyl)-piperazin-1-yl]-4-oxo-1,4-dihydrobenzo-[b][1,8]naphthyridine-3-carboxylate in 32 cm³ of acetic acid and 32 cm³ of 17.5% aqueous hydrochloric acid solution. 2.7 g of 7,8-difluoro-1-(2,4-difluorophenyl)-4-oxo-1,4-dihydrobenzo[b][1,8]naphthyridine-3-carboxylic acid were obtained in the form of a yellow solid melting at about 318–320° C.

Ethyl 1-(2,4-difluorophenyl)-7-fluoro-8-[4-(4-fluorophenyl)piperazin-1-yl]-4-oxo-1,4-dihydrobenzo[b][1,8]naphthyridine-3-carboxylate was obtained under the conditions of Example 13, but from 3.68 g of ethyl 3-(2-chloro-6,7-difluoro-3-quinolyl)-2-dimethylaminomethylene-3-oxopropionate and 3.87 g of 2,4-difluoroaniline in 40 cm³ of trichloromethane. 50 cm³ of ethanol and 1.5 cm³ of 1,8-diazabicyclo[5.4.0]undec-7-ene were added to the mixture, which was heated at a temperature around 80° C. for approximately 1 hour. After cooling to a temperature around 10° C., the product was filtered off and washed 2 times with 50 cm³ of ethanol and 2 times with 50 cm³ of isopropyl ether. 3.3 g of ethyl 1-(2,4-difluorophenyl)-7,8-difluoro-4-oxo-1,4-dihydro-benzo[b][1,8]naphthyridine-3-carboxylate were obtained in the form of a yellow solid melting at approximately 300° C., which solid was used without additional purification in the subsequent stages.

Ethyl 3-(2-chloro-6,7-difluoro-3-quinolyl)-2-dimethylaminomethylene-3-oxopropionate is disclosed in European Patent No. EP 431,991.

EXAMPLE 17

8-[(Cyclohexyl)(ethyl)amino]-7-fluoro-1-methyl-4-oxo-1,4-dihydrobenzo[b][1,8]naphthyridine-3-carboxylic Acid:

8-[(Cyclohexyl)(ethyl)amino]-7-fluoro-1-methyl-4-oxo-1,4-dihydrobenzo[b][1,8]naphthyridine-3-carboxylic acid was prepared from 0.5 g of ethyl 8-cyclohexylamino-7-fluoro-1-methyl-4-oxo-1,4-dihydrobenzo[b][1,8]naphthyridine-3-carboxylate, 0.19 cm³ of iodoethane, 0.096 g of sodium hydride as a 60% dispersion in mineral oil and 10 cm³ of dimethylformamide. After treatment with 10 cm³ of water and 2 cm³ of 1N hydrochloric acid, the mixture was extracted 3 times with 20 cm³ of trichloromethane. The combined organic phases were washed 1 time with 20 cm³ of water, dried over magnesium sulphate and concentrated under reduced pressure (20 kPa) at a temperature around 40° C. 0.25 g of 8-[(cyclohexyl)(ethyl)amino]-7-fluoro-1-methyl-4-oxo-1,4-dihydrobenzo[b][1,8]naphthyridine-3-carboxylic acid was obtained in the form of a yellow solid melting at about 230° C.

Ethyl 8-cyclohexylamino-7-fluoro-1-methyl-4-oxo-1,4-dihydrobenzo[b][1,8]naphthyridine-3-carboxylate was prepared under the conditions of Example 4, but from 3 g of ethyl 7,8-difluoro-1-methyl-4-oxo-1,4-dihydrobenzo[b][1,8]naphthyridine-3-carboxylate and 2.2 cm³ of cyclohexylamine in 30 cm³ of dimethyl sulphoxide. After filtering 2 times with 15 cm³ of ethanol, 3.3 g of ethyl 8-cyclohexylamino-7-fluoro-1-methyl-4-oxo-1,4-dihydrobenzo[b][1,8]naphthyridine-3-carboxylate were obtained in the form of a yellow solid melting at about 220° C.

The present invention is also directed to pharmaceutical compositions which can be used in human or veterinary medicine which comprise, as active product, at least one compound of general formula (I) in the pure state (in the free form or in the salt form) or in the form of a combination with one or more compatible and pharmaceutically acceptable diluents or adjuvants. These compositions can be used by the topical route.

The compositions for topical administration can be, for example, creams, ointments, gels, lotions, liniments or aerosols. They can also be pulverulent solid compositions. They may also be intended for nasal administration.

When the compositions are creams, ointments or gels, these compositions can be, for example, hydrophilic ointments comprising, for example, polyethylene glycols and appropriate amounts of water, or hydrophobic ointments comprising, for example, petroleum jelly, liquid paraffin, vegetable oils or animal fats, synthetic glycerides, waxes or liquid polyalkylsiloxanes. They can also be hydrophilic creams comprising oil-in-water emulsifying agents, such as, for example, sodium or triethanolamine soaps, fatty alcohols, sulphated fatty alcohols or polysorbates, optionally in combination with water-in-oil emulsifying agents, or hydrophobic creams comprising water-in-oil emulsifying agents, such as wool grease, sorbitan esters or monoglycerides. They can also be hydrophilic gels based on gelled water, gelled alcohol, gelled glycerol or gelled propylene glycol, or hydrophobic gels comprising liquid paraffin to which polyethylene has been added or fatty oils gelled with colloidal silicon oxide or aluminium or zinc soaps.

By way of example, when the compositions are aerosols, for use in the form of liquid aerosols, the compositions can be stable sterile solutions or solid compositions dissolved at the time of use in pyrogen-free sterile water, in saline or any other pharmaceutically acceptable vehicle; for use in the form of dry aerosols intended to be directly inhaled, the active principle is finely divided and combined with a water-soluble solid diluent or vehicle with a particle size of 30 to 80 μm, for example dextran, mannitol or lactose.

In human or veterinary therapeutics, the compositions according to the invention are useful in the prophylactic or curative treatment of cutaneomucosal infections of Gram-positive bacterial origin, for example, curative treatment of cutaneous infections due to Gram-positive bacteria and/or preventive treatment of infections due to multiresistant Gram-positive bacteria, for example in the treatment of infections associated with wounds, grafts or burns, in the treatment of infections related to skin lesions, or in the treatment of impetigos and furonculoses, as well as for the prevention of the contamination of the nasal passageways by multiresistant Gram-positive bacteria and also for decontamination with a view to avoiding the dissemination of these microorganisms.

The physician will generally determine the dosage which he considers the most appropriate according to the age, the stage of the infection and the other factors specific to the subject to be treated. The active principle is generally present at about 1 or about 2% in the formulation. This formulation is applied 1 to 3 times daily by the topical route.

The following example, given without implied limitation, illustrates a composition according to the invention:

EXAMPLE

A cream with a dose of about 2% of free acid was prepared, according to the usual techniques, having the following composition:

| | |
|---|---|
| Choline 7-fluoro-8-[4-(4-fluorophenyl)-piperazin-1-yl]-1-methyl-4-oxo-1,4-dihydrobenzo[b][1,8]naphthyridine-3-carboxylate | 2.52 mg |
| Cetomacrogol | 30.0 mg |
| Benzyl alcohol | 3.0 mg |
| Water for Injections | 100 mg |

Furthermore, the compounds of general formula (I) can also be used as agents for preserving or disinfecting organic or inorganic substances, for example in the dye, fats, paper, wood or polymer industries or in the textile industry, the food industry or for the treatment of water. It is also understood that compositions including a compound of general formula (I) in the pure state or in the form of a combination with compatible diluents or adjuvants is also within the scope of the present invention.

We claim:
1. A benzo[b][1,8]naphthyridine compound of the formula (I):

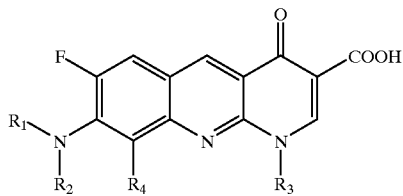  (I)

in which:
R$_1$ and R$_2$, which are identical or different, represent:
an alkyl or cycloalkyl radical having 3 to 8 members,
or R$_1$ and R$_2$ form, together with the nitrogen atom to which they are attached, a 6-membered heterocycle optionally having one more nitrogen atom, which, when present, is substituted at the 4-position by:
a phenyl radical,
a phenyl radical substituted by a halogen atom or by an alkylthiomethyl radical,
a benzyl radical,
a benzyl radical substituted by a halogen atom,
a heterocyclylmethyl radical, the heterocyclyl part of which is saturated or unsaturated and has 5 or 6 members,
a phenylamino radical, the phenyl part of which is optionally substituted by a halogen atom,
or R$_1$ and R$_2$ form, together with the nitrogen atom to which they are attached, a 7-membered heterocycle, optionally having one more nitrogen atom, which, when present, is substituted by one of the above-listed substituents of the 6-membered heterocycle;
or R$_1$ and R$_2$ form, together with the nitrogen atom to which they are attached, an 8-membered heterocycle, optionally having one more nitrogen atom, which may be optionally substituted by one of the above-listed substituents of the 6-membered heterocycle;

R$_3$ represents:
an alkyl radical,
a fluoroalkyl radical,
a carboxyalkyl radical,
a cycloalkyl radical having 3 to 6 carbon atoms,
a fluorophenyl radical,
a difluorophenyl radical,
an alkyloxy radical, or
an alkylamino radical; and
R$_4$ represents a hydrogen atom or a fluorine atom,
wherein the abovementioned alkyl radicals are straight or branched and has 1 to 4 carbon atoms;
or a stereoisomeric form thereof, a mixture of stereoisomeric forms thereof, a metal salt, an addition salt with a nitrogenous base, or an acid addition salt thereof.

2. The benzo[b][1,8]naphthyridine compound according to claim 1, wherein:
R$_1$ and R$_2$, which are identical or different, represent:
an alkyl radical having 1 or 2 carbon atoms, or
a cyclopropyl radical,
or R$_1$ and R$_2$ form, together with the nitrogen atom to which they are attached, a 6-membered heterocycle, optionally having one more nitrogen atom, which, when present, is substituted at the 4-position by:
a phenyl radical,
a phenyl radical substituted by a halogen atom or by a methylthiomethyl radical,
a benzyl radical,
a benzyl radical substituted by a halogen atom,
a heterocyclylmethyl radical, the heterocyclyl part of which is unsaturated and has 5 members, or
a phenylamino radical, the phenyl part of which is optionally substituted by a halogen atom,
or R$_1$ and R$_2$ form, together with the nitrogen atom to which they are attached, a 7- or 8-membered heterocycle;

R$_3$ represents:
an alkyl radical having 1 or 2 carbon atoms,
a cyclopropyl radical,
a difluorophenyl radical, or
a methylamino radical; and
R$_4$ represents a hydrogen atom or a fluorine atom;
or a stereoisomeric form thereof, a mixture of stereoisomeric forms thereof, a metal salt, an addition salt with a nitrogenous base, or an acid addition salt thereof.

3. The benzo[b][1,8]naphthyridine compound according to claim 1, wherein said compound is 7-fluoro-8-[4-(4-fluorophenyl)piperazin-1-yl]-1-methyl-4-oxo-1,4-dihydrobenzo[b][1,8]naphthyridine-3-carboxylic acid or an acid addition salt thereof.

4. A process for preparing a benzo[b][1,8]naphthyridine compound as claimed in claim 1, said process comprising reacting an amine of formula (II):

  (II)

with a benzo[b][1,8]naphthyridine of formula (III):

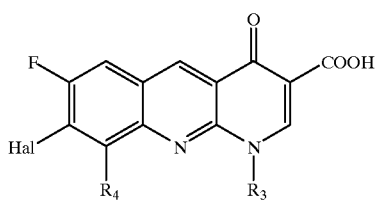  (III)

wherein R$_1$, R$_2$, R$_3$ and R$_4$ are defined as in claim 1, Hal is a fluorine, chlorine or bromine atom when R$_4$ is a hydrogen atom, or Hal and R$_4$ are simultaneously fluorine atoms.

5. The process according to claim 4, said process further comprising reacting said benzo[b][1,8]naphthyridine compound with a suitable agent to form a metal salt, an addition salt with a nitrogenous base or an acid addition salt thereof.

6. A process for preparing a benzo[b][1,8]naphthyridine compound as claimed in claim 1, said process comprising converting an ester of formula (IV):

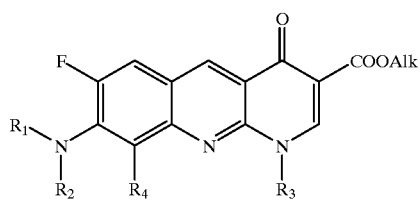  (IV)

into a benzo[b][1,8]naphthyridine compound of formula (I), wherein $R_1$, $R_2$, and $R_4$ are defined as in claim 1, $R_3$ is defined as in claim 1 or represents a protected alkylamino radical, and Alk is a straight or branched alkyl radical having 1 to 4 carbon atoms.

7. The process according to claim 6, wherein, when the $R_3$ radical of the ester of formula (IV) represents a protected alkylamino radical, said process further comprises removing the protecting group from said alkylamino radical.

8. The process according to claim 6, said process further comprising reacting said benzo[b][1,8]naphthyridine compound with a suitable agent to form a metal salt, an addition salt with a nitrogenous base, or an acid addition salt thereof.

9. The process according to claim 7, said process further comprising reacting said benzo[b][1,8]naphthyridine compound with a suitable agent to form a metal salt, an addition salt with a nitrogenous base, or an acid addition salt thereof.

10. A composition comprising at least one compound as claimed in claim 1, and optionally one or more compatible diluents or adjuvants.

11. A pharmaceutical composition comprising at least one compound as claimed in claim 1, and optionally one or more compatible and pharmaceutically acceptable diluents or adjuvants.

12. A composition comprising the compound as claimed in claim 3, and optionally one or more compatible diluents or adjuvants.

13. A pharmaceutical composition comprising the compound as claimed in claim 3, and optionally one or more compatible and pharmaceutically acceptable diluents or adjuvants.

14. A method for the prophylactic or curative treatment of an infection, comprising administering to a patient in need thereof an antibacterially effective amount of a compound as claimed in claim 1, wherein the infecting organism is a gram-positive microorganism.

15. A method for the prophylactic or curative treatment of an infection, comprising administering to a patient in need thereof an antibacterially effective amount of a compound as claimed in claim 1, wherein the infecting organism is quinolone-resistant.

16. A method for the prophylactic or curative treatment of an infection, comprising administering to a patient in need thereof an antibacterially effective amount of a compound as claimed in claim 1, wherein the infecting organism is a *Staphylococcus aureus* strain.

17. A method for the prophylactic or curative treatment of an infection, comprising administering to a patient in need thereof an antibacterially effective amount of a compound as claimed in claim 2, wherein the infecting organism is a gram-positive microorganism.

18. A method for the prophylactic or curative treatment of an infection, comprising administering to a patient in need thereof an antibacterially effective amount of a compound as claimed in claim 2, wherein the infecting organism is quinolone-resistant.

19. A method for the prophylactic or curative treatment of an infection, comprising administering to a patient in need thereof an antibacterially effective amount of a compound as claimed in claim 2, wherein the infecting organism is a *Staphylococcus aureus* strain.

20. A method for the prophylactic or curative treatment of an infection, comprising administering to a patient in need thereof an antibacterially effective amount of a compound as claimed in claim 3, wherein the infecting organism is a gram-positive microorganism.

21. A method for the prophylactic or curative treatment of an infection, comprising administering to a patient in need thereof an antibacterially effective amount of a compound as claimed in claim 3, wherein the infecting organism is quinolone-resistant.

22. A method for the prophylactic or curative treatment of an infection, comprising administering to a patient in need thereof an antibacterially effective amount of a compound as claimed in claim 3, wherein the infecting organism is a *Staphylococcus aureus* strain.

* * * * *